United States Patent [19]

Unger

[11] 4,144,595
[45] Mar. 20, 1979

[54] ARTIFICIAL HEART CHAMBER

[76] Inventor: Felix Unger, Mohsgasse 4, Vienna 3, Austria

[21] Appl. No.: 743,069

[22] Filed: Nov. 18, 1976

[30] Foreign Application Priority Data

Nov. 27, 1975 [AT] Austria .................................. 9044/75

[51] Int. Cl.$^2$ ........................... A61F 1/24; A61M 1/03
[52] U.S. Cl. ....................................... 3/1.7; 128/1 D; 417/395
[58] Field of Search ......... 3/1.7, 1; 128/1 D, DIG. 3; 417/395, 394, 413

[56] References Cited

U.S. PATENT DOCUMENTS

| 3,553,736 | 1/1971 | Kantrowitz et al. | 3/1.7 |
| 3,568,214 | 3/1971 | Goldschmied | 3/1.7 |

OTHER PUBLICATIONS

"A Psuedoendocardium for Implantable Blood Pumps" by D. Liotta et al., Transactions American Society for Artificial Internal Organs, vol. XII, 1966, pp. 129-134.
"Thrombus Generation Within the Artificial Heart" by D. B. Olsen et al., The Journal of Thoracic and Cardiovascular Surgery, vol. 70, No. 2, Aug. 1975, pp. 248-254.

*Primary Examiner*—Ronald L. Frinks
*Attorney, Agent, or Firm*—Toren, McGeady and Stanger

[57] ABSTRACT

An artificial heart chamber is structured with a nondeformable housing, with valves being provided in the housing for admitting and ejecting blood from the chamber, the valves including valve openings which communicate with the chamber. A diaphragm is mounted within the chamber for movement through an operating cycle including an ejection phase whereby blood is ejected from the chamber through one of the valves. The diaphragm is actuated through its operating cycle by fluid pressure means and during the ejection phase of the operating cycle of the diaphragm, the diaphragm forms a cupola. The invention is particularly directed toward the arrangement of the diaphragm within the chamber whereby the cupola formed during the ejection phase of the diaphragm operating cycle comes to lie beneath the valve openings of the valves and whereby, as a result of the diaphragm arrangement, no dead water zones are formed during the operating cycle of the diaphragm.

5 Claims, 5 Drawing Figures

ARTIFICIAL HEART CHAMBER

BACKGROUND OF THE INVENTION

The present invention relates to prosthetic devices generally and more particularly to artificial heart mechanisms. Specifically, the invention is concerned with an artificial heart chamber which is structured with a nondeformable housing having valves for admitting and ejecting blood from the chamber. The heart chamber of the type to which the present invention relates is equipped with a diaphragm arranged within the housing with the diaphragm being moved into one end position by fluid pressure means actuating diaphragm movement from one side thereof.

Heart chambers of the type to which the present invention relates are known and by way of example, reference is made to "The Journal of Thoracic and Cardiovascular Surgery", vol. 70, page 248-255 (1975) the authors of which are D. Olsen and F. Unger et al. Reference is also had to "European Surgical Research", vol. 8, pages 105-116 (1976) whose authors are F. Unger, D. Olsen et al. It has been found, however, that these known artificial heart chambers involve essential drawbacks in their use and operation. It has been found that with known artificial heart prosthesis spaces may develop wherein no currents will occur so that there may be formed thrombi with subsequent thrombosis resulting therefrom. Furthermore, the residual volume, i.e. the difference between the filling volume and the ejected volume, in such devices, is relatively great. Thus, the outer dimensions of such known devices cannot be kept advantageously small as may be desired and they tend to require overly large dimensions.

Furthermore, the diaphragm which is used in devices of the known types will be flexed during its rhythmic or cyclical operation so that there will always be present the danger of rupture or break of the diaphragm.

Finally, due to the unfavorable arrangement of cardiac valves in devices of the known types, filling conditions generally tend to be poor with the result that a vacuum is required for the filling phase of operation.

The present invention is directed toward elimination of the drawbacks of presently known artificial heart chambers and is particularly aimed toward avoidance of the risk of thrombosis in such chambers.

Furthermore, the invention is aimed at provision of a heart chamber having minimum outer dimensions.

SUMMARY OF THE INVENTION

Briefly, the present invention may be described as an artificial heart chamber comprising a nondeformable housing, valve means in the housing for admitting and ejecting blood from the chamber, said valve means including valve openings communicating with the chamber, a diaphragm mounted within the chamber for movement through an operating cycle including an ejection phase whereby blood is ejected from the chamber through the valve means, and fluid pressure means for actuating the diaphragm through its operating cycle.

The diaphragm acts during the ejection phase of its operating cycle to form a cupola. The invention is particularly directed toward the arrangement of the diaphragm within the housing so that no dead water zones will be formed during the operation of the diaphragm and so that the cupola of the diaphragm formed during the ejection phase will come to lie directly beneath the valves of the chamber.

By avoiding the formation of dead water zones, stagnation of the blood is prevented so that the threat of thrombosis is practically eliminated. Due to the fact that the cupola of the diaphragm comes to lie directly beneath the cardiac valves during the ejection phase of operation of the diaphragm, the residual volume of the chamber of the present invention will be relatively small and as a result the overall outer dimensions of the device of the present invention can consequently be kept relatively small.

By one aspect of the present invention, the reduction of the overall outer dimensions of the device will be further enhanced by virtue of the fact that the heart chamber is designed in the form of an ellipsoid.

By another aspect of the present invention, the housing is formed with an upper part and a lower part with the inner layer of the upper part and the diaphragm being integrally formed from the same plastic material so that the two parts have a continuously concavely smooth extending configuration one into the other at the equator of the ellipsoid. As a result, the dead water zones are positively avoided by this particular phase of the invention.

By another aspect of the invention, the heart chamber of the present invention is formed with a base member which is connected at the equator of the ellipsoid with the upper part of the housing and which has at the junction with the housing a toroidal reinforcement which is covered by the plastic material of the housing upper part. The plastic used for the upper part of the housing is of a soft elastic material and the materials of the housing and of the toroidal reinforcement may be cemented with each other. As a result, the specific structure of the invention involved in this aspect thereof serves to increase the working time of the heart chamber.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there is illustrated and described a preferred embodiment of the invention.

DETAILED DESCRIPTION OF THE PREFERRED EMBODIMENT

Figure 1A:
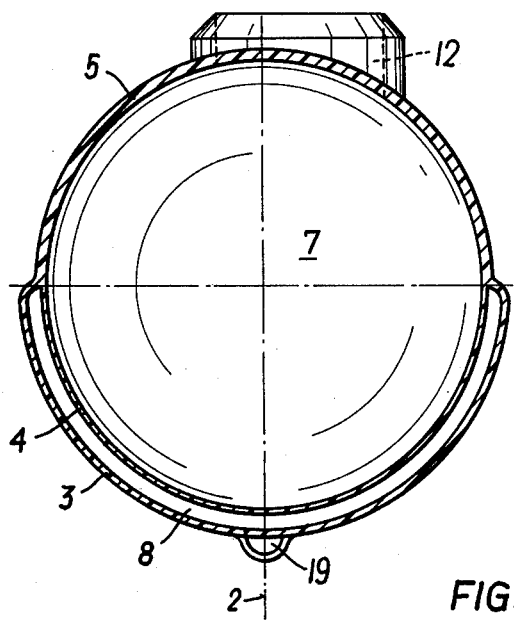
FIG. 1a is a schematic cross sectional view taken through the heart chamber according to the present invention showing the chamber in a condition where it is filled with blood (end diastole)
Figure 1B:
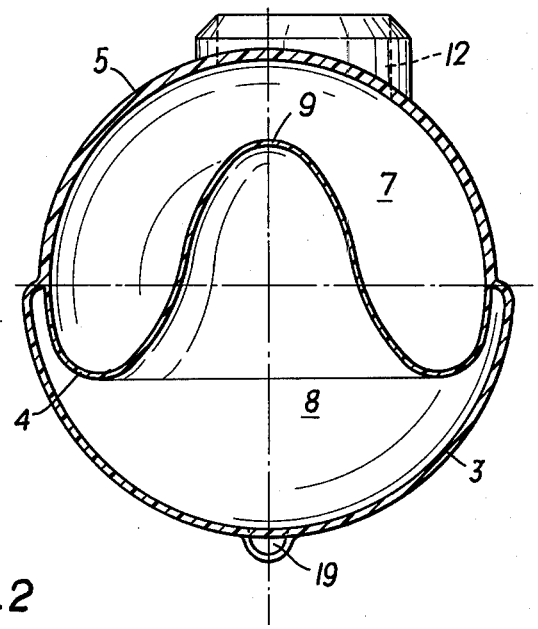
FIG. 1b is a schematic sectional view showing the same heart chamber in the ejection phase of its operating cycle (systole)
Figure 2:
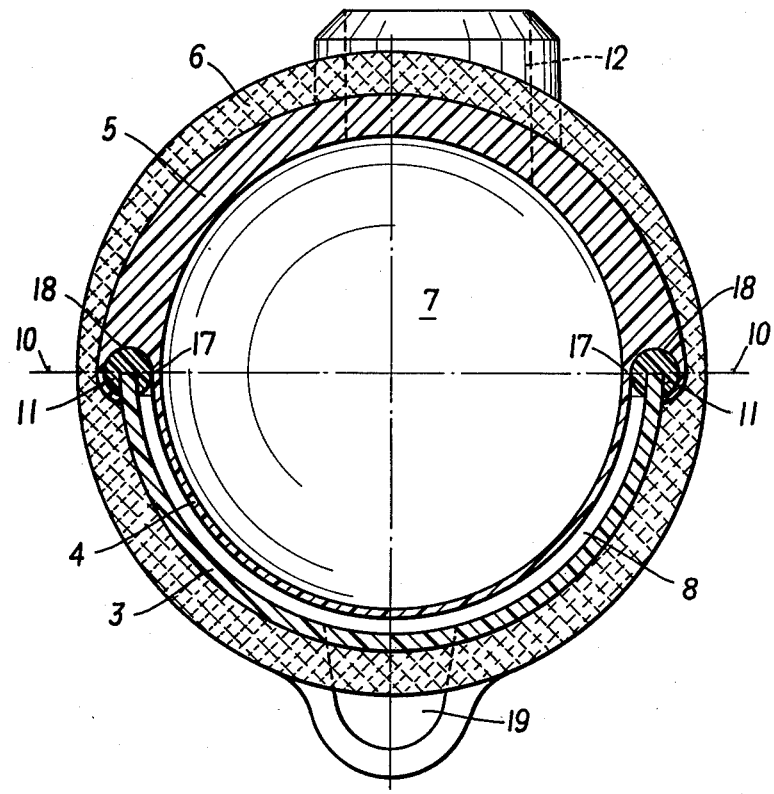
FIG. 2 is a cross sectional view showing the structure of the heart chamber according to the present invention.
Figure 3:
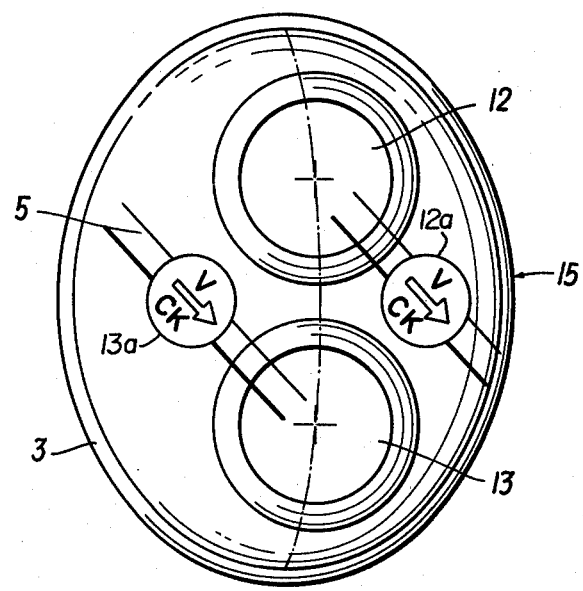
FIG. 3 is a schematic view which shows the arrangement of the inlet and outlet openings of the chamber.

Referring now to the drawings wherein like reference numerals are used to refer to similar parts throughout the various figures thereof, there is shown in FIGS. 1a and 1b an artificial heart chamber in accordance with the present invention which consists of a nondeformable upper part 5 and a nondeformable heart base 3. Interiorly of the heart chamber there is provided a diaphragm 4 made of resilient or elastic material which adjoins the upper part 5 and which is exteriorly surrounded by the heart base 3.

In the lower region of the heart base 3 and arranged tangentially thereto there is provided an inlet opening 19 which operates to permit flow of a fluid under pressure, for example, air. When the pressure fluid enters a chamber 8 formed between the heart base 3 and the diaphragm 4, the diaphragm will be moved in response to the pressure created within the chamber 8. When the pressure is increased within the chamber 8, the diaphragm 4 will be moved upwardly or toward the upper part of the chamber 5 in which case the blood which may be contained within a blood chamber 7 will be ejected through an outlet opening 12 in communication with a check valve 12a, which is arranged together with an inlet opening 13 in communication with a check valve 13a, in the upper region of the upper housing part 5.

The diaphragm 4 will function to move through an operating cycle which includes an ejection phase where blood is ejected from the chamber 7. The ejection phase of the operating cycle of the diaphragm is depicted in FIG. 1b. When the diaphragm 4 moves in its ejection phase of operation, the diaphragm will assume a curved configuration to form a cupola with the cupola being formed in such a way that as a result of the particular arrangement of the diaphragm in accordance with the present invention the diaphragm cupola will come to lie directly beneath the opening 12, 13 of the valve means which permit admission and ejection of the blood from within the chamber 7. The filling of the chamber 7 is effected in the subsequent phase of the operation of the diaphragm 4 by the weight of the blood itself, with the fluid chamber 8 being brought into contact either with the outside air or with a vacuum source.

The artificial heart chamber in accordance with the present invention is designed and shaped as an ellipsoid 15.

The diaphragm 4 and the heart base 3 are connected with the upper housing part 5 in the range of an equator 10 which is the equator of the ellipsoid of the chamber or housing of the present invention. At the junction point between the upper part 5 and the diaphragm 4 there occurs a continuity of shape and it will be seen that the diaphragm 4 is formed so as to extend continuously concavely smooth with the upper part 5. In this manner, dead water zones are avoided and, as a result, the possibility of the formation of thrombi is eliminated. The heart chamber of the present invention is produced by forming a cast of a polymer (e.g. Silastic D RTV which is available from Dow Corning Corporation) with the cast being produced within a metallic mold in the form of an ellipsoid. Into the mold there is poured a positive hollow mold of a fusable polymer (e.g. Epolene available from Eastman Kodak Company). This mold is then dipped repeatedly into a polymer until a sufficient layer thickness is obtained (e.g. 8 layers of Avcothane made by Avco Everrett of Massachusetts). The upper half of the polymeric ellipsoid forms the inner surface of the upper housing part 5 and the lower half forms the finished diaphragm 4. The heart base 3 is then attached to the device and the heart base 3 likewise consists of a polymeric plastic which is provided at its ends with a toroidal reinforcement 11 so that the toroidal reinforcement embraces the ellipsoid within the range of the equator 10. The toroidal reinforcement can be produced in the form of a tube which is attached to the heart base 3 made of a material which will not combine with the material of the upper part, i.e. the Silastic of Dow Corning.

Subsequently, the retaining rings for the heart valves are placed upon the openings provided within the housing and then the polymer of which the upper part and the diaphragm 4 consists is applied again on the upper part 5 so that the toroid 11 of the heart base 3 will be sufficiently covered. After this, the entire body is reinforced with a layer 6 of fabric bandages and plastic so that it is practically nondeformable. Finally, the fusable inner mold is melted in a warming cabinet and the molten polymer can issue through the valve openings. The valves may now be inserted in place.

The plastic material for the upper part and for the diaphragm 4 should be of soft elastic and the heart base should consist of a nondeformable material. Both materials may be of the type which can be cemented with each other. When the diaphragm 4 curves during its ejection phase, it will form a bend as indicated at 17. However, the stress produced at this point will spread through the elastic material of the upper part 5 up to point 18. The risk of breakage or rupture at the point 17 is thus avoided to a great extent. In the blood-filled state of the heart chamber, the diaphragm will be stressed only by tensile forces.

The centers of the openings 12 and 13 through which blood is admitted and ejected from the valves of the chamber are arranged upon the meridian of the ellipsoid, which is the line of intersection of the plane of symmetry 2 with the ellipsoid. This has the effect that the cupola 9 of the diaphragm formed in the plane of symmetry comes to lie beneath the openings 12 and 13.

In a heart chamber in accordance with the present invention utilized during testing procedures, the following dimensions were found to be useful. An ellipsoid having an outside length of 8.6 cm and a thickness of 6.2 cm. With valve retaining rings, the total height is 7.5 cm. The valve centers have a distance of 4 cm. The filling volume is 220 cc, and the maximum ejection volume is 178 cc with the maximum circulation volume being 15.8 l/min.

With a pump pressure of 0.3 excess at a frequency of 90 beats / min. and an arterial pressure of 100 mm Hg and 0 mm Hg auricular pressure, the cardiac output was 9.4 l/min. If the auricular pressure is increased to 20 mm Hg, the cardiac output increases to 13.6 l/min.

Set forth in Table 1 below are additional measured results at various auricular and arterial pressures. The values were obtained with a pump pressure of 0.3 excess at a vacuum of 5 mm Hg, a beat frequency of 90/min. The second phase of ventricular systole was 200 ms.

Figure 4:
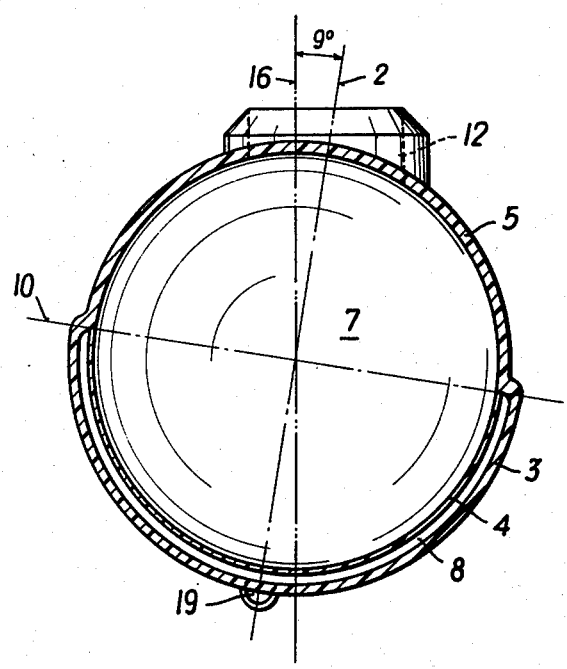
FIG. 4 is a schematic cross sectional view similar to the view of the FIG. 1 showing the heart chamber of the invention with one of the openings thereof in the installation state.

The heart chamber according to the present invention can be used both as a heart substitute and for the assistance of circulation both paracorporeally (externally) and implanted (internally). When implanted as a heart substitute, the right ventricle will come to lie in front of the left ventricle. As shown in FIG. 4, the plane of symmetry 2 is inclined by 9° toward the vertical 16.

TABLE I

| Cardiac output (l/min) at different auricular and arterial pressures | | | | | |
|---|---|---|---|---|---|
| Auricular Pressure mg Hg | | 0 | 5 | 10 | 15 | 20 |
| Arterial Pressure mm Hg | 70 | 10.1 | 11.2 | 12.0 | 12.6 | 13.8 |
| | 100 | 9.4 | 10.8 | 11.4 | 12.2 | 13.6 |
| | 130 | 8.3 | 9.6 | 10.6 | 11.8 | 12.8 |

While a specific embodiment of the invention has been shown and described in detail to illustrate the application of the inventive principles, it will be understood that the invention may be embodied otherwise without departing from such principles.

What is claimed is:

1. An artificial heart assembly comprising: a nondeformable housing;

valve means in said housing for admitting and ejecting blood to and from said artificial heart assembly;

diaphragm means mounted in said assembly for movement through an operating cycle between an end diastolic position and an end systolic position to pump blood to and from said artificial heart assembly; and fluid pressure means for continuously actuating said diaphragm through said operating cycle;

said diaphragm being structurally joined with said housing to form together with a part of said housing an inner wall surface defining within said artificial heart assembly a blood chamber within which blood is received and from which blood is emitted during actuation of said diaphragm through said operating cycle, said diaphragm and said part of said housing being arranged to define said inner wall surface in the form of an ellipsoid that is continuously concavely smooth throughout when said diaphragm is in said end diastolic position.

2. An artificial heart assembly according to claim 1 wherein during movement of said diaphragm toward said end systolic position said diaphragm acts to form a cupola with the arrangement of said diaphragm being such that said cupola thus formed comes to lie beneath said valve means to eliminate formation of dead water zones within said blood chamber during the operating cycle of said diaphragm.

3. An artificial heart assembly according to claim 1 wherein said nondeformable housing is formed in two parts consisting of an upper part and a base part, said upper part being said part of said housing which forms together with said diaphragm said inner wall surface, said upper part and said diaphragm being structured as an integral unit made of the same plastic material arranged in a continuously extending form to define said inner wall surface as a smooth continuous surface.

4. An artificial heart assembly according to claim 3 wherein said ellipsoid includes an equator and wherein said upper part and said base part of said nondeformable housing are connected at said equator of said ellipsoid by a toroidal reinforcement which is covered by said plastic material of said upper part of said housing, said plastic material of said upper part being of a soft elastic material with the plastic used for the housing and for the toroidal reinforcement being cemented with each other.

5. An artificial heart assembly according to claim 1 wherein said nondeformable housing is reinforced by means of fabric layers.

* * * * *